(12) United States Patent
Rentier et al.

(10) Patent No.: US 7,112,331 B2
(45) Date of Patent: Sep. 26, 2006

(54) VACCINES AGAINST VARICELLA ZOSTER VIRUS GENE 63 PRODUCT

(75) Inventors: Bernard Rentier, Liege (BE); Catherine Sadzot, Liege (BE)

(73) Assignees: SmithKline Beecham Biologicals, s.a., (BE); University of Liege, (BE)

( * ) Notice: Subject to any disclaimer, the term of this patent is extended or adjusted under 35 U.S.C. 154(b) by 0 days.

(21) Appl. No.: 09/865,637

(22) PCT Filed: Feb. 4, 1997

(86) PCT No.: PCT/EP97/00520

§ 371 (c)(1), (2), (4) Date: Oct. 20, 1998

(87) PCT Pub. No.: WO97/28820

PCT Pub. Date: Aug. 14, 1997

(65) Prior Publication Data

US 2001/0041183 A1 Nov. 15, 2001

Related U.S. Application Data

(62) Division of application No. 09/117,711, filed on Oct. 20, 1998, now abandoned.

(30) Foreign Application Priority Data

Feb. 9, 1996 (GB) .................................... 9602617
Dec. 24, 1996 (GB) .................................... 9626882

(51) Int. Cl.
*A61K 39/25* (2006.01)
*A61K 48/00* (2006.01)

(52) U.S. Cl. ...................... 424/230.1; 514/44
(58) Field of Classification Search ............. 424/230.1, 424/229.1, 231.1; 514/44; 536/23.72; 435/235.1, 435/236

See application file for complete search history.

(56) References Cited

U.S. PATENT DOCUMENTS 5,306,635 A 4/1994 Keller et al.

FOREIGN PATENT DOCUMENTS

| EP | 0 244 155 | 11/1987 |
|---|---|---|
| EP | 0 405 867 | 1/1991 |
| WO | WO 94/00153 | 6/1994 |

OTHER PUBLICATIONS

Nader et al. Journal of Enfectious Diseases 7:13-17, 1995.*
Kinchington et al. Journal of Virology 69:4274-4282, 1995.*
Debrus et al. Journal of Virology 69:3240-3245, May 1995.*
Dunkel et al. Neurology 45 (suppl 8): S21-S22, 1995.*
USP27 NF22. The United States Pharmacopeia, The National Formulary, 2004. United States Pharmacopeial Convention, Inc. , Rockville, MD. pp. 2628-2636, 1949-1951.*
Liu et al (Clinical Biochemistry 30:455-463, 1997).*
Wicks et al (Human Gene Therapy 6 (3): 317-323, abstract only cited).*
Debrus et al., "Varicella-Zoster Virus Gene 63 Encodes an Immediate-Early Protein That is Abundantly Expressed during Latency", Journal of Virology, May 1995, p. 3240-3245.
Phelan, et al., "A herpes simples virus type 1 immediate-early gene product, IE63, regulated small nuclear ribonucleoprotein distribution", *Proc. Natl. Acad. Sci. USA*, 90: 9056-9060 (1993).
Kennedy, et al., "Down-Regulation of Glial Fibrillary Acidic Protein Expression during Acute Lytic Varicella-Zoster Virus Infection of Cultured Human Astrocytes", *Virology*, 205: 558-562 (1994).
Paul R. Kinchington, et al., "The Transcriptional Regulatory Proteins Encoded by Varicella-Zoster Virus Open Reading Frames (ORF's) 4 and 63, but Not ORF 61, Are Associated with Purified Virus Particles," Journal of Virology, Jul. 1995 vol. 69 p. 4274-4282.

* cited by examiner

*Primary Examiner*—Mary E. Mosher
(74) *Attorney, Agent, or Firm*—Jason C. Fedon; Edward R. Cimmi; Charles M. Rinzig

(57) ABSTRACT

The present invention relates to compositions for the treatment or prevention of Zoster of individuals infected with Varicella Zoster virus (VZV), and to the prevention and treatment of Varicella infections. The compositions of the invention comprise the protein encoded by VZV gene 63 or an immunologically active derivative thereof. The invention further relates to compositions containing DNA or RNA corresponding to VZV gene 63.

9 Claims, 3 Drawing Sheets

VACCINES AGAINST VARICELLA ZOSTER VIRUS GENE 63 PRODUCT

Figure 1:
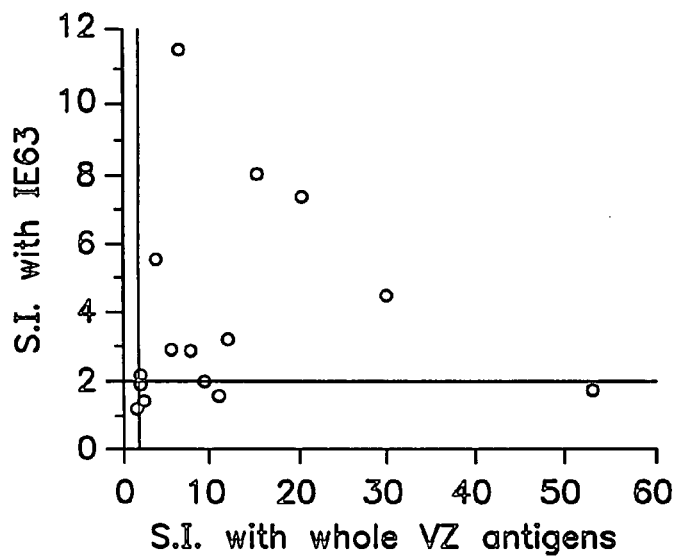

This is a divisional of application Ser. No. 09/117,711 filed Oct. 20, 1998 now abandoned which is a 371 of International Application No. PCT/EP97/00520 filed 04 Feb. 1997; which claims priority of Great Britain Application Nos. GB 9602617.4 filed 09 Feb. 1996 and GB 9626882.6 filed 24 Dec. 1996.

The present invention relates to compositions for the treatment or prevention of Zoster of individuals infected with Varicella Zoster virus (VZV), and to the prevention and treatment of Varicella infections. The compositions of the invention comprise the protein encoded by VZV gene 63 or an immunologically active derivative thereof. The invention further relates to compositions containing DNA or RNA corresponding to VZV gene 63.

Varicella Virus is a human alpha herpes virus which causes two human diseases: on primary infection VZV causes childhood chicken pox (Varicella) thereafter the virus becomes latent and frequently reactivates (often decades later) to produce shingles (Zoster). During chicken pox, the virus penetrates the peripheral nervous system where it remains latent until reactivates as the painful Zoster form. Whilst the virus is latent the expression of most viral genes are repressed. It is believed that cell mediated immunity plays a crucial role in the control of latency, since reactivation as Zoster (or shingles) is frequent in the elderly or in immunocompromised individuals.

VZV infection is characterized by minimal presence of free virus. During latency and reactivation virus is mainly intracellular. Accordingly, recurrent disease is not prevented even by high levels of neutralizing antibodies and virus control depends on cell mediated immunity. In order to obtain protection by vaccination, it is therefore desirable to induce not just an antibody response, but also a CTL response. An effective vaccine should prime CTL capable of acting as early as possible as soon as signs of reactivation of latent virus appear.

As the mechanism of antigen recognition by Cytotoxic T lymphocytes CTL involves breakdown of native antigen into peptides, binding of the proteolytic fragments to MHC molecules and export of the complex to the cell surface, any virus coded polypeptide not just those that are integral membrane proteins like the glycoproteins, can be a potential targets of T cell mediated responses. However since the VZV genome codes for several non structural proteins and internal virion proteins. in addition to external glycoproteins, this results in a large number of potential CTL targets and it is not known which protein would be the most relevant.

The genome of VZ virus is composed of 71 open reading frames, encoding 68 proteins. The sequence of the virus DNA is known (J. Gen Virol 67 1759–1816). The Varicella Zoster virus gene 63 encodes an Immediate early protein with a predicted molecular mass of 30.5 kDa (Debrus et al, J. of Virology 69(5), 1995 p 3240). The gene starts at 110581 (START CODON) and goes through to 111414 (STOP CODON). Another copy of the gene in reverse orientation is found between base 119316 to 118483. Rather unusually the IE 63 protein has been shown to be expressed in a rat model, in neurons during latency. The protein has been expressed as a fusion protein in E.coli (Debrus et al).

It has now been discovered that VZV IE 63 protein is detected exclusively in the cytoplasm of neurons of latently infected human trigeminal and thoracic ganglia. This is the first identification of an alpha-herpesvirus protein expressed during latency in the human nervous system.

Furthermore, the inventors have discovered that this protein is an important target for the immune system, in particular is a target of a T cell response and thus is useful in the prevention and treatment of VZV infections. In particular, in the prevention of Zoster in patients already infected with VZV.

Accordingly, the present invention provides a pharmaceutical composition comprising Varicella Zoster Virus IE63 protein or immunlogically functional equivalent thereof and a pharmaceutically acceptable carrier.

This is the first medical use for such a protein and thus the invention accordingly provides the VZV IE63 protein or an immunologically functional equivalent derivative thereof for use in medicine.

In a further aspect of the invention there is provided a method of treating a human susceptible to or suffering from VZV infection, which comprises administering a safe and effective amount of a composition according to the invention.

The amount of protein in each vaccine dose is selected as an amount which induces an immunoprotective response without significant, adverse side effects in typical vaccines. Such amount will vary depending upon which specific immunogen is employed and how it is presented. Generally, it is expected that each dose will comprise 1–1000 μg of protein, preferably 2–100 μg, most preferably 4–40 μg. An optimal amount for a particular vaccine can be ascertained by standard studies involving observation of appropriate immune responses in subjects. Following an initial vaccination, subjects may receive one or several booster immunisation adequately spaced.

In addition to vaccination of persons susceptible to VZV infections, the pharmaceutical compositions of the present invention may be used to treat, immunotherapeutically, patients suffering from VZV infections, in order to prevent or significantly decrease recurrent disease, frequency, severity or duration of shingles episodes.

In the vaccine of the invention, an aqueous solution of the VZV IE63 protein(s), can be used directly. Alternatively, the VZV IE63 protein(s), with or without prior lyophilization, can be mixed together or with any of the various known adjuvants. Such adjuvants include, but are not limited to, aluminum hydroxide, muramyl dipeptide and saponins such as Quil A, in particular QS21 or 3 Deacylated monophosphoryl lipid A (3D-MPL). Adjuvants or adjuvant systems that preferentially induce a TH1 response are preferred. Adjuvants which are capable of preferential stimulation of the TH1 cell response are described in International Patent Application Nos. WO 94/00153 and WO 95/17209.

A particular preferred adjuvant comprises QS21, an Hplc purified non-toxic fraction derived from the bark of Quillaja Saponaria Molina, and 3 De-O-acylated monophosphoryl lipid A (3 D-MPL), optionally together with an oil in water emulsion.

3 De-O-acylated monophosphoryl lipid A is known from GB 2220211 (Ribi). Chemically it is a mixture of 3 De-O-acylated monophosphoryl lipid A with 4, 5 or 6 acylated chains and is manufactured by Ribi Immunochem Montana. A preferred form of 3 De-O-acylated monophosphoryl lipid A is disclosed in International Patent Application No. 92/16556.

QS21 is a Hplc purified non toxic fraction of a saponin from the bark of the South American tree Quillaja Saponaria Molina and its method of its production is disclosed (as QA21) in U.S. Pat. No. 5,057,540.

A preferred oil-in-water emulsion comprises a metabolisible oil, such as squalene, alpha tocopherol and tween 80. Additionally the oil in water emulsion may contain span 85 and/or lecithin.

The ratio of QS21:3D-MPL will typically be in the order of 1:10 to 10:1; preferably 1:5 to 5:1 and often substantially 1:1. The preferred range for optimal synergy is 2.5:1 to 1:1 3D MPL:QS21. Typically for human administration QS21 and 3D MPL will be present in a vaccine in the range 1 µg–100 µg, preferably 10 µg–50 µg per dose. Typically the oil in water will comprise from 2 to 10% squalene, from 2 to 10% alpha tocopherol and from 0.3 to 3% tween 80. Preferably the ratio of squalene:alpha tocopherol is equal or less than 1 as this provides a more stable emulsion. Span 85 may also be present at a level of 1%. In some cases it may be advantageous that the vaccines of the present invention will further contain a stabiliser.

As a further exemplary alternative, the protein can be encapsulated within microparticles such as liposomes. In yet another exemplary alternative, the VZV IE63 protein(s) can be conjugated to an immunostimulating, macromolecule, such as killed *Bordetella* or a tetanus toxoid.

Vaccine preparation is generally described in New Trends and Developments in Vaccines, Voller et al. (eds), University Park Press, Baltimore. Md., 1978. Encapsulation within liposomes is described by Fullerton, U.S. Pat. No. 4,235,877. Conjugation of proteins to macromolecules is disclosed, for example, by Likhite, U.S. Pat. No. 4,372,954 and Armor et al., U.S. Pat. 4,474,757. Use of Quil A is disclosed by Dalsgaard et al., *Acta Vet Scand,* 18:349 (1977). 3D-MPL is available from Ribi immunochem, USA, and is disclosed in British Patent Application No. 2220211 and U.S. Pat. No. 4,912,094. QS21 is disclosed in U.S. Pat. No. 5,057,540.

The use of polynucleotide of the invention in genetic immunisation will preferably employ a suitable delivery method such as direct injection of plasmid DNA into muscles (Wolff et al., Hum Mol Genet 1992. 1:363, Manthorpe et al., Hum. Gene Ther. 1963:4, 419), delivery of DNA complexed with specific protein carriers (Wu et al., J Biol Chem 1989:264, 1985), coprecipation of DNA with calcium phosphate (Benvenisty & Reshef, PNAS, 1986:83 ,9551), or with other facilitators encapsulation of DNA in various forms of liposomes (Kaneda et al., Science 1989: 243,375), particle bombardment (Tang et al., Nature 1992, 356:152, Eisenbraun et al., DNA Cell Biol 1993, 12:791) and in vivo infection using cloned retroviral vectors (Seegar et al, PNAS 1984:81.5849) or non-infectious, recombinant viral vectors, such as Semliki Forest helper 2 system (Berglund) et al Bio/Technology 1993, 11:916–920. Suitable promoters for muscle transfection include CMV, RSV, Sra, actin, MCK, alpha globin, adenovirus and dihydrofolate reductase. A preferred way of delivery a polynucleotide in accordance with the invention utilitises gold particles delivered by means of a gene gun U.S. Pat. No. 5,100,792. U.S. Pat. No. 5,036,006, and 4,945,050.

The polynucleotide compositions of the invention may be administered using the dosages and routes of administration described in WO 90/11092. It will be apparent however that the precise dosage will depend on factors such as the weight, sex, mode of administration, general health of the patient and the condition to be treated. Nonetheless for Intramuscular use the dosages to employed will typically be in the range of 0.05 μg/kg to about 50 mg/kg, more typically from about 0.1 to 10 mg/kg. Subcutaneous, epidermal, intradermal or mucosal administration may be advantageous, due to the ability to induce high levels of CTL.

The vaccine of the present invention may additionally contain other antigenic components such as VZV gpI, gpII, gpIII, gpIV or gpV or their truncated derivatives or other immediate early proteins such as IE62 protein. In particular truncated gpI, gpII or gpIII as disclosed in European Patent application published under No. 0405867.

In a preferred embodiment of the present invention there is provided a vaccine composition comprising an anchorless gpI in combination with IE63 or IE63 derivative.

By anchorless it is meant, a VZV glycoprotein derivative which is devoid of substantially all of the C-terminal anchor region and which allows for secretion on when expressed in mammalian cells. Such proteins are described in EP-A-0405867.

In an alternative embodiment there is provided a vaccine comprising a fusion protein comprising an amino acid sequence embodying IE 63 or derivative and amino acid sequence embodying one of gpI, gpII, gpIII, gpIV or gpV or derivative thereof or other immediate early protein, such as IE62.

In an alternative embodiment, a ploynucleotide capable of expressing IE 63 or derivative thereof may be used directly as a nucleic acid vaccine. Preferably the polynucledtide is DNA. In such cases, the polynucleotide will be under the control of a suitable promoter.

RNA immunisation may also be used. RNA in such cases, may be prepared in accordance with the methods of WO92/10578.

BRIEF DESCRIPTION OF THE FIGURES

FIG. 1. Stimulation Index (S.I.) obtained after stimulation with whole VZ antigens or with IE63. T lymphocyte stimulation was determined by stimulation of PBMC (Peripheral Blood Mononucles cytes) isolated by ficollhypaque centrifugation. The stimulation index (SI) was calculated as the ratio of CPM in protein stimulated wells versus control wells, and was considered as positive if greater than 2.

FIG. 2. PBMC from 19 healthy adults were assayed for T cell proliferation in response to stimulation with either VZV antigens or GST-IE63 purified protein. When S.I. after VZV stimulation were plotted and compared to the S.I. with GST-IE63, the two non immune patients appeared clearly negative (S.I. less than 2.0) with both antigen preparations.

FIG. 3. When T cell populations recovered by T-Lymphokwik were used, the lysis of targets expressing VZV proteins was significantly higher than the one observed for the uninfected or control targets as demonstrated for one assay.

FIG. 4. The RCF of CD8+ cells recognizing IE62 or IE63 was 28500.+-.10100 SE and 30500.+-.13700 SE respectively, which was not statistically different (p=0,9), indicating that both viral proteins were recognized with the same efficiency by CD8+ cells.

EXAMPLE 1

Vaccine Formulation Comprising VZV IE 63 Protein

The two adjuvant formulations are made each comprising the following oil in water emulsion component.

SB 62:5% squalene 5% tocopherol 2.0% tween 80; the particle size was 180 nm

1(a) Preparation of Emulsion SB62 (2 Fold Concentrate)

Tween 80 is dissolved in phosphate buffered saline (PSB) to give a 2% solution in the PBS. To provide 100 ml two fold concentrate emulsion 5 g of DL alpha tocopherol and 5 ml of squalene are vortexed to mix thoroughly. 90 ml of PBS/Tween solution is added and mixed thoroughly. The resulting emulsion is then passed through a syringe and finally microfluidised by using an M110S microfluidics machine. The resulting oil droplets have a size of approximately 180 nm.

1(b) The Antigen is Prepared According to the Method of Debrus et al (supra).

1(c) Preparation of IE63 Protein QS21/3D MPL Oil in Water Formulation.

To the emulsion of 1 a) an equal volume of twice concentrated antigen (either 20 μg or 100 μg) is added and mixed. This is combined with 50 μg/ml of 3D-MPL and 20 μg/ml of QS21 to give the final formulation. Buffer is according to salt content and pH.

EXAMPLE 2

Immunological Characteristics of IEP63

2.1 Materials

Blood was drawn from eleven healthy donors of whom one had been vaccinated. All these donors were adults, with a history of chickenpox during childhood. In each case, 30 ml of blood were harvested in heparinised tubes and 5 ml were kept for clotting in order to harvest serum.

2.2 Humoral Immune Response

Elisa tests were performed using whole VZV and control antigens to detect anti-VZV IgGs in blood samples: all the donors tested (except one) had detectable level of anti VZV antibodies, thus providing a serologic evidence of chickenpox developed during childhood.

We searched for the presence of anti-IE63 antibodies, by a Western Blot analysis in which IE63, cloned in pGEX5X and expressed in *E.coli* as a fusion protein (GST-IE63) and purified by affinity chromatography (Debrus et al, J. Virol, 69, 3240–3245) was used. The GST protein, expressed and purified in the same manner was used as a negative control. In all the blood sample tested, the purified IE63 fusion protein was recognised indicating the presence of anti-IE63 antibodies in the serum. The control protein was never recognised by the antibodies.

2.3 Cellular Immune Response

T lymphocyte stimulation was determined by stimulation of PBMC (Peripheral Blood Mononucles cytes) isolated by ficollhypaque centrifugation.

All assays were performed in triplicates by stimulation of $3 \times 10^5$ PBMC with PHA (phytohemagglutinin) to determine the non specific stimulation index, whole VZV and control antigens (prepared by sonication of infected or uninfected melanoma cells) and purified fusion protein (GST-IE63 or GST alone). On day 6, cells were pulsed with $^3$H-Thymidine for 16 hours, and then harvested. The stimulation index (SI) was calculated as the ratio of CPM in protein stimulated wells versus control wells, and was considered as positive if>2.

2.4 T cells Proliferation Results:

10 proliferation assays have been performed so far, with the parameters previously determined.

The results are listed in table 1.

The S.I. obtained after stimulation with whole VZ antigens or with IE63 have been plotted on a graph which is shown as FIG. 1.

From these data, we can conclude that:

Most people (6/10) have a memory T cell response to VZV IE63

Two donors have a very low SI with both whole antigens and purified fusion protein and could be considered as negative (SI<2). However, one of these had a very low antibody titer, without any clear evidence of chickenpox history and could therefore be a negative donor. The other one, whose antibody titer was high, had a better SI while the assay was performed with MBP-IE63 (SI=3.4), indicating that in some cases, one of the fusion proteins was better recognised by the T cells and that a comparison of both proteins could be useful in the cases where SI are very low, with a high standard deviation.

Two other donors presented a negative response to IE63 while the SI with whole antigens was high, but the stimulation was done only with GST fusion protein.

EXAMPLE 3

Cellular Responses

Figure 2:
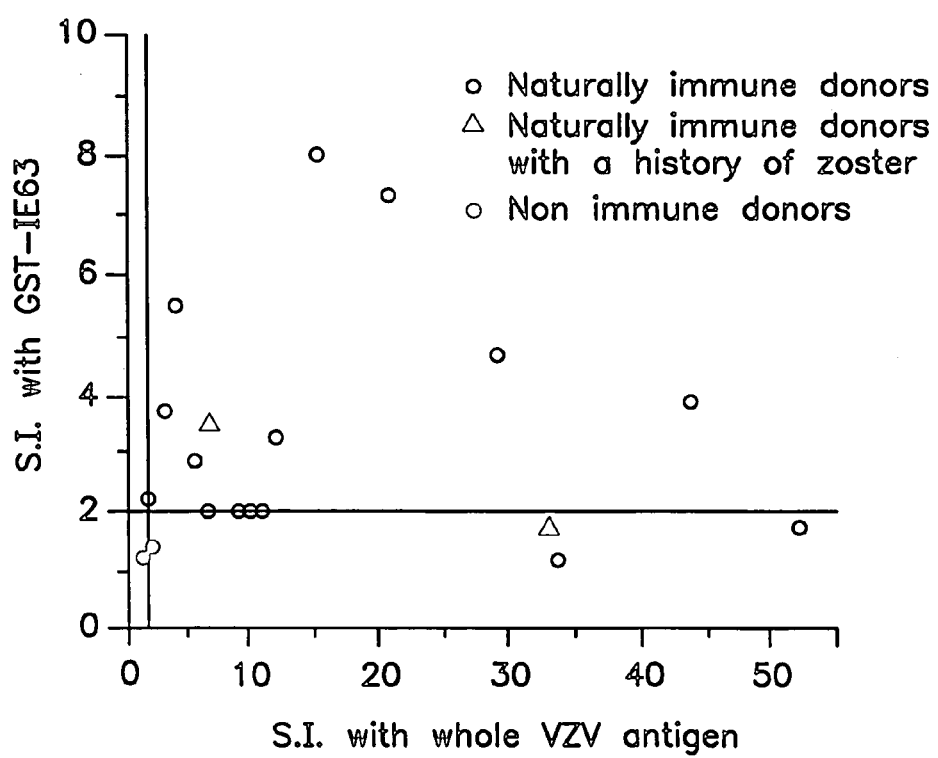

In an expansion of the above experiment, PBMC from 19 healthy adults were assayed for T cell proliferation in response to stimulation with either VZV antigens or GST-IE63 purified protein. The mean S.I. with VZ antigens was 15.5±3.3 SE with values between 2.1 and 52. This means S.I. after stimulation by GST-IE63 was 3.4±0.48 SE with value between 1.8 and 8. These S.I. data were significantly higher than those observed for non immune patients whose S.I. was 1.95±0.48 SE for VZV antigens and 1.3±0.1 SE for IE63. When S.I. after VZV stimulation were plotted and compared to the S.I. with GST-IE63, the two non immune patients appeared clearly negative (S.I<2.0) with both antigen preparations (FIG. 2). All 17 immune donors had a S.I. to VZV antigens higher than 2.0. Among these positive donors, 3 (17%), of whom one had a history of multiple zoster eruptions, presented a very strong response to VZV antigens, while the S.I. with GST-IE63 was below 2.0. Four donors had a S.I. of 2.0 for GST-IE63 with a S.I. for VZ antigens ranging from 5.4 to 11. However, all these donors with a S.I. with GST-IE63≦2 had a very important response to GST alone (data not shown), which made it difficult to interpret the results. All the other natural immune individuals (59%) presented a strong response to GST-IE63, with a S.I. between 2.3 and 8. However, no correlation was found between the stimulation with VZ antigens and with the fusion protein.

EXAMPLE 4

Cytokine Assays

The cytokine production by PBMC stimulated by IE63 was evaluated for 7 subjects: PBMC were stimulated either by GST or GST-IE63 and IL.2, IL4 and g-FN were deetected on day 2, 4 or 6 by ELISA. The results were expressed as the difference between the concentration of cytokines detected after stimulation by GST-IE63 or GST alone. IL2 and IL4 have never been detected while γ-IFN was produced in significant amount (175 to 1400 pg/ml) by the T-cells stimulated by IE63, with a maximum produced on day 4. The amount of γ-IFN detected in the culture where no stimulation was observed was significantly lower:

| Donor | T-cell proliferation to GST-IE63 (S.I.) | IFN-γ (pg/ml) | IL4 (pg/ml) |
|---|---|---|---|
| 1 | 2, 9 | 750 | 0 |
| 2 | 2, 2 | 1400 | 0 |
| 3 | 7, 4 | 500 | 0 |
| 4 | 8, 0 | 625 | 0 |
| 5 | 2, 0 | 175 | 0 |
| 6 | 2, 0 | 50 | 0 |

EXAMPLE 5

Cytotoxicity Assays

IE62 and IE63-specific CTL responses were detected in limiting dilution assays of T cells obtained from 10 VZV-immune donors. These assays were performed with autologous targets either non infected or infected by vaccinia-control, vaccinia-IE62 or vaccinia-IE63. The background generated by control targets presented a wide range of variation among the donors, but results were considered as valid only if the lysis of virus-specific targets was at least 10% higher than the lysis with control targets (uninfected or infected with vaccinia-control).

Figure 3:
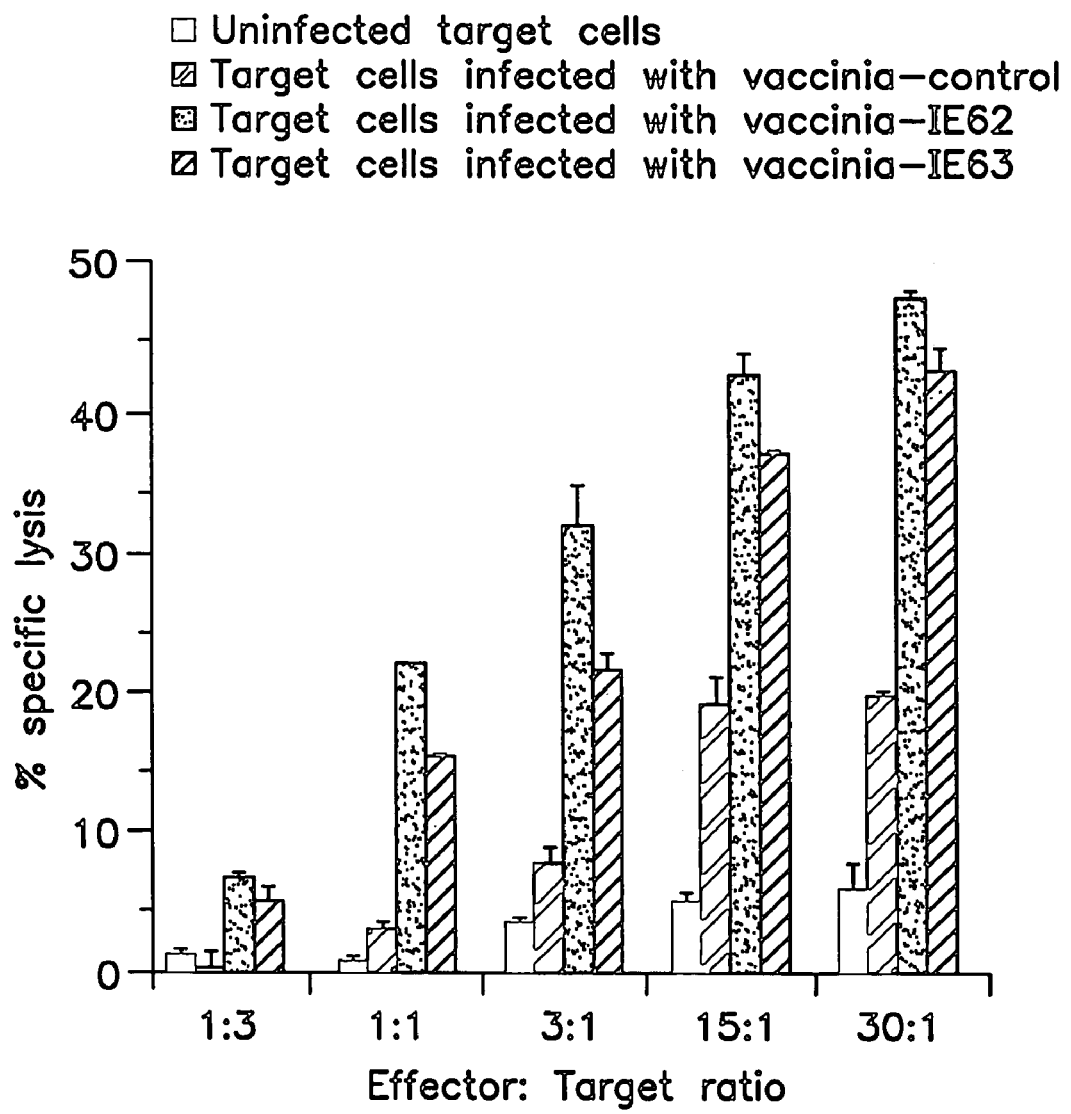

When T cell populations recovered by T-Lymphokwik were used, the lysis of targets expressing VZV proteins was significantly higher than the one observed for the uninfected or control targets as demonstrated for one assay (FIG. 3). The lysis observed with targets expressing IE62 was not significantly different from the lysis with targets expressing IE63. Similar results were obtained for the 4 assays performed with whole T cell population: a specific lysis of 25 to 48% was observed for IE62 and 27 to 43% for IE63. The mean precursor frequency for T cells that recognised IE62 or IE63 was 44500±22500 SE and 31000±16000 SE respectively, but the difference was not statistically significant (p=0.8).

Figure 4:
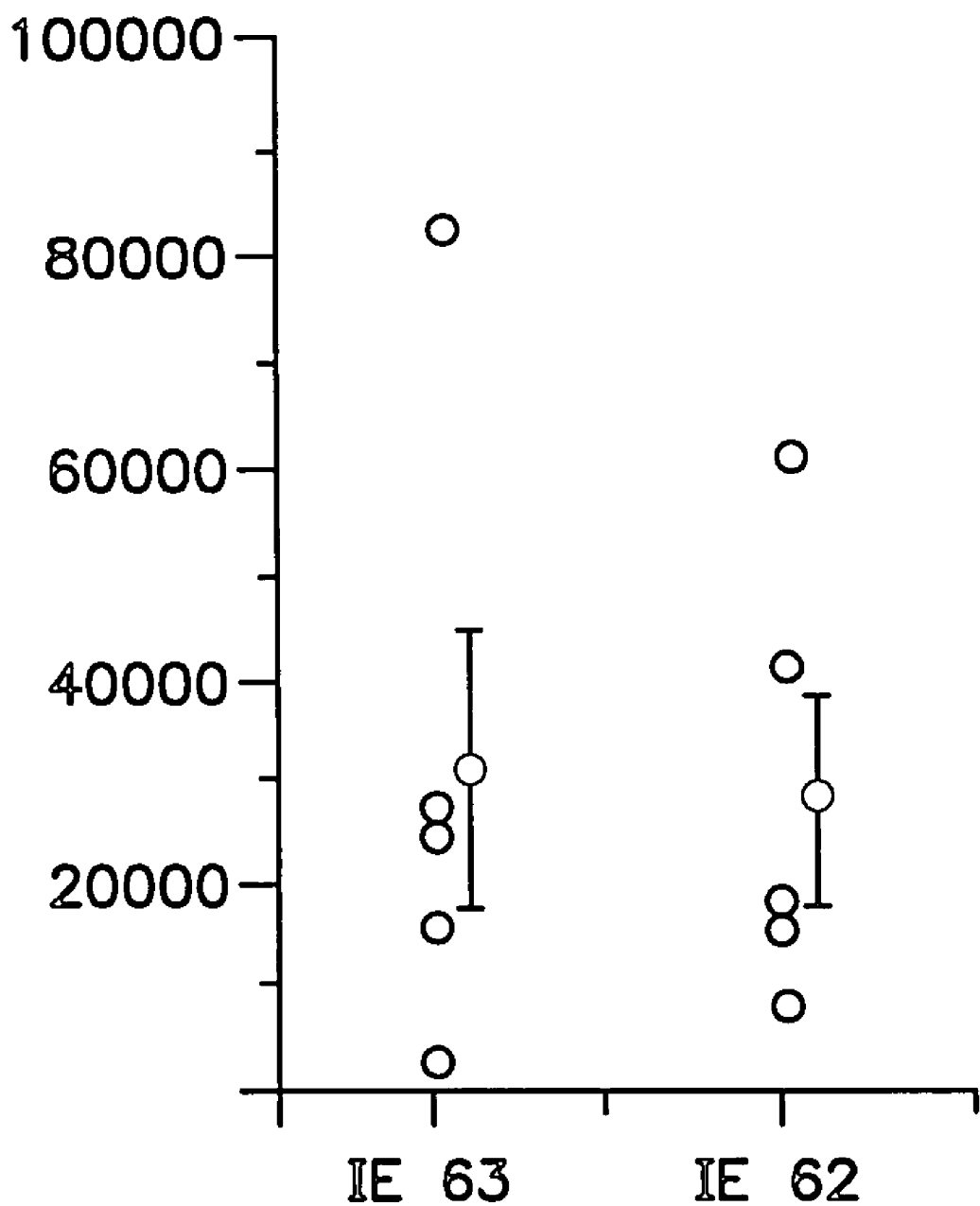

Limiting dilution cultures were also prepared using purified populations of CD4+ and CD8+ T lymphocytes as effectors. Both populations lysed IE62 and IE63-targets. The RCF of CD8+ cells recognising IE62 or IE63 was 28500±10100 SE and 30500±13700 SE respectively, which was not statistically different (p=0,9), indicating that both viral proteins were recognised with the same efficiency by CD8+ cells (FIG. 4). The number of cells lysing IE63 targets was also the same in both populations of effectors cells: the mean CD4+ effectors cells was 31450±7500 SE which is the same as the frequency of CD8+ cells (P=0,97). However, the calculation of the CD4+ cell frequency for IE62 recognition has been rejected by the computerised analysis.

EXAMPLE 6

VZV IE63 Expression During Latency

To analyse VZV expression in latently-infected ganglia, one trigeminal and multiple thoracic ganglia from 9 adults and 3 infants were obtained within 24 hours after death. None of the subjects was immunocompromised before death, and at autopsy, there were no cutaneous signs of recent herpesvirus infection. Enzyme immunoassay revealed antibody to VZV in serum of all the adults. Serum available from only one of the 3 infants did not contain antibody to VZV. Liquid PCR amplification using VZV-specific primers (Mahalingham R et al Engl. J. Med 323 627–631) revealed VZV DNA in all adult ganglia, but not in any infant ganglia in DNA extracted from a small portion of each ganglion. The remaining portions of each ganglion were analysed immunohistochemically using antibodies raised in rabbit against the 30.5-kD-VZV IE63 protein, expressed as a glutathione-S-transferase fusion protein in E.coli and purified as described (Debrus et al supra). VZV infected and uninfected BSC-1 (African monkey kidney) cells served as positive and negative controls respectively.

In VZV-infected BSC-1 cells, two focal areas of typical VZV cytopathology containing VZV IE63 protein were seen. No signal was detected in uninfected cells or in HSV-infected BSC-1 cells. In ganglia acquired 17 h after death from a 46-year old man who died of atherosclerosis, a characteristic red colour revealed VZV IE63 protein exclusively in the cytoplasm of 3 neurons. No signal was detected when normal rabbit serum was applied to an adjacent section of the same ganglion. Intense red staining was detected in the cytoplasm of a neuron in adjacent sections of a different thoracic ganglion of the same subject. A lighter red colour was also often seen in multiple neurons of latently-infected ganglia, suggesting a more diffuse, perhaps lower abundance infection. The red VZV IE63 protein-specific staining was never seen in satellite (capsular) cells, capillaries, connective tissue, nerve fascicles within the ganglia, or nerve rootless entering the ganglia. No signal was detected when the antiserum against VZV IE63 protein was applied to ganglia of a 2-month-old infant who died of sepsis complicating a congenital omphalocele and pulmonary hypoplasia. Overall, VZV IE63 protein was found in 5 ganglia (4 thoracic and 1 trigeminal) from 2 adults. In one of these adults, VZV IE63 protein was detected in all 10 sections from 4 of 5 thoracic ganglion. In the second adult, VZV IE63 protein was detected in all 4 sections from the trigeminal ganglion. In positive sections, VZV IE63 protein was detected in the cytoplasm of 2–4 neurons. VZV IE protein was not detected in any of 4 sections prepared from each of 16 ganglia from 7 other adults, or in any of 4 sections from each of 9 ganglia from 3 infants.

The detection of VZV DNA in nearly all ganglia but VZV IE63 protein only in some latently-infected ganglia might reflect sampling, ie analysis of every section of each ganglion containing VZV DNA for VZV IE63 protein might have revealed additional positive ganglia. Alternatively, virus expression might differ in different ganglia, for example, in ganglia latently infected with HSV, the number of neurons containing HSV DNA is far greater than that revealing latency-associated transcripts.

Finally, virus reactivation might have occurred, although this seems unlikely in the subjects who ganglia contained VZV IE63 protein, since there was no clinical evidence of zosterioform rash before death, no history of prolonged neuralgic pain which may precede rash (prehaerpetic neuralgia), no history of deermatomal distribution pain without rash (Zoster sine herpete), and no history of postherpetic neuralgia suggesting a low grade ganglionitis. Furthermore, histologic examination of ganglia revealed no neuronophagia, inclusion bodies or an inflammatory response.

CONCLUSIONS

From these experiments, we can conclude that VZV IE63 elicits a complete immune response:
  anti-IE63 antibodies can be detected by western blot analysis in the serum of most donors with a history of chickenpox;

T cells can proliferate after in vitro stimulation by IE63 (purified as a GST-fusion protein), but the limited number of tested donors did not allow to find a direct correlation between the stimulation index (S.I.) with VZV and the one with IE63. The T-cells proliferating in response to IE63 stimulation are mostly Th1 as indicated by the expression of high amount of IFN-gamma in the supernatant;

a T cell cytotoxic activity in the context of IE63 recognition has been shown. CD4+ as well as CD8+ cells participate in the lysis process, as determined by the use of purified effector cells. The number of precursor cells recognising IE63 is similar to the number of cells responding to IE62.

This is the first report of the identification of a herpesvirus protein expressed during latency in the human nervous system taken together with its immunological properties, it is an excellent antigen to be included in vaccine against Varicella Zoster.

TABLE 1

T CELL PROLIFERATION

|     |               |     | S.I. with whole Ag |         | S.I. with GST-IE63 |
| --- | ------------- | --- | ------------------ | ------- | ------------------ |
| CS: | Ab status     | :4  | −41                | 5 ug    | 1.9                |
|     | EIA: >1024    | :16 | 6.4                | 2.5 ug  | 1.5                |
|     |               | :64 | 5.7                | 1.25 ug | 3.2                |
|     |               | PHA | 11.5               | 0.6 ug  | 11.6               |

|     |               |     | S.I. |         | S.I. |
| --- | ------------- | --- | ---- | ------- | ---- |
| MS: | Ab status     | :4  | 7.5  | 5 ug    | 1.1  |
|     | EIA: >1024    | :16 | 11.9 | 2.5 ug  | 2.7  |
|     |               | :64 | 5.9  | 1.25 ug | 3.2  |
|     |               | PHA | 8.1  | 0.6 ug  | 2.5  |
| VD  | Ab status     | :4  | 4.3  | 5 ug    | 2.9  |
|     | EIA: >1024    | :16 | 4.5  | 2.5 ug  | 1.3  |
|     |               | :64 | 5.5  | 1.25 ug | 1.5  |
|     |               | PHA | 12.6 | 0.6 ug  | 1.1  |
| JM  | Ab status     | :4  | 1.5  | 5 ug    | 1.7  |
|     | EIA: >1024    | :16 | 2.1  | 2.5 ug  | 1.4  |
|     |               | :64 | 2.0  | 1.25 ug | 2.2  |
|     |               | PHA | 7.1  | 0.6 ug  | 0.9  |
| CD  | Ab status     | :4  | 4.0  | 5 ug    | 4.3  |
|     | EIA: >1024    | :16 | 20.1 | 2.5 ug  | 2.8  |
|     |               | :64 | 8.6  | 1.25 ug | 7.4  |
|     |               | PHA | 25.8 | 0.6 ug  | 4.4  |
| CL  | Ab status     | :4  | 7.0  | 5 ug    | 1.0  |
|     | EIA: 256      | :16 | 7.0  | 2.5 ug  | 2.0  |
|     |               | :64 | 9.0  | 1.25 ug | 2.0  |
|     |               | PHA | 22.0 | 0.6 ug  | 2.0  |
| J   | Ab status     | :4  | 7.0  | 5 ug    | 1.0  |
|     | EIA: 256      | :16 | 7.0  | 2.5 ug  | 2.0  |
|     |               | :64 | 9.0  | 1.25 ug | 2.0  |
|     |               | PHA | 22.0 | 0.6 ug  | 2.0  |
| DJ  | Ab status     | :4  | 6.5  | 5 ug    | nd   |
|     | EIA: >1024    | :16 | 2.1  | 2.5 ug  | nd   |
|     |               | :64 | −5.1 | 1.25 ug | nd   |
|     |               | PHA | 24.0 | 0.6 ug  | nd   |
| SH  | Ab status     | :4  | 1.4  | 5 ug    | 0.8  |
|     | EIA: 16       | :16 | 2.1  | 2.5 ug  | 1.2  |
|     | WB: ?         | :64 | 0.4  | 1.25 ug | 1.5  |
|     |               | PHA | 23.4 | 0.6 ug  | 1.9  |
| LZ: | Ab status     | :4  | 15.0 | 5 ug    | 4.0  |
|     | EIA: >1024    | :16 | 14.0 | 2.5 ug  | 8.0  |
|     |               | :64 | 11.0 | 1.25 ug | 8.0  |
|     |               | PHA | 38.0 | 0.6 ug  | 8.0  |
| R:  | Ab status     | :4  | 13.0 | 5 ug    | 3.6  |
|     | non available | :16 | 23.4 | 2.5 ug  | 3.4  |
|     | non available | :64 | 5.2  | 1.25 ug | 2.6  |
|     |               | PHA | 30.9 | 0.6 ug  | 3.8  |
| V:  | Ab status     | :4  | 0.9  | 5 ug    | 0.6  |
|     | non available | :16 | 1.1  | 2.5 ug  | 1.1  |
|     | non available | :64 | 0.7  | 1.25 ug | ???  |
|     | PHA           | I   | 23.5 | 0.6 ug  | 0.7  |
| E:  | Ab status     | :4  | 28.2 | 5 ug    | 0.7  |
|     | EIA: >1024    | :16 | 9.1  | 2.5 ug  | 1.8  |
|     |               | :64 | 52.6 | 1.25 ug | 1.2  |
|     |               | PHA | 46.7 | 0.6 ug  | 0.6  |
| G:  | Ab status     | :4  | 2.4  | 5 ug    | 1.2  |
|     | EIA: <16      | :16 | 2.3  | 2.5 ug  | 0.9  |
|     |               | :64 | 1.3  | 1.25 ug | 1.4  |
|     |               | PHA | 70.9 | 0.6 ug  | 1.4  |

TABLE 1-continued

| | | | T CELL PROLIFERATION | | |
|---|---|---|---|---|---|
| M: | Ab status | :4 | 6.1 | 5 ug | 2.7 |
| | EIA:>1024 | :16 | 23.4 | 2.5 ug | 3.2 |
| | | :64 | 29.6 | 1.25 ug | 2.3 |
| | | PHA | 79.5 | 0.6 ug | 4.6 |
| C: | Ab status | :4 | 0.8 | 5 ug | 0.5 |
| | EIA: <16 | :16 | 1.6 | 2.5 ug | 0.9 |
| | | :64 | 1.4 | 1.25 ug | 1.0 |
| | | PHA | 113.6 | 0.6 ug | 1.2 |
| Z: | Ab status | :4 | 1.5 | 5 ug | 0.9 |
| | EIA: <16 | :16 | 0.7 | 2.5 ug | 1.2 |
| | | :64 | 0.7 | 1.25 ug | 0.6 |
| | | PHA | 9.3 | 0.6 ug | ??? |

Table 1:Humoral and Cellular Immune Response in Response to VZV. S.I. was measured after stimulation of whole antigens (sonicated infected or mock infected melanoma cells diluted 4, 16 or 64 times) or with IE63 fusion protein (GST or GST-IE63).

The humoral immunity status has been evaluated by ELISA with whole antigen (expressed as the dilution for which O.D. is>0.250) or by Western blot analysis with IE63.

The invention claimed is:

1. A method of treating a patient suffering from or susceptible to Varicella Zoster virus infection, comprising administering to a patient a pharmaceutical composition comprising an isolated Varicella Zoster Virus IE63 protein and a pharmaceutically acceptable excipient, wherein the composition induces a humoral or cellular immune response without significant, adverse side effects.

2. A method of treating a patient suffering from or susceptible to Varicella Zoster virus infection, comprising administering to a patient a pharmaceutical composition comprising an isolated nucleic acid encoding IE63, wherein the composition induces a humoral or cellular immune response without significant, adverse side effects.

3. A method of treating a patient suffering from or susceptible to Varicella Zoster virus infection as claimed in claim 1, additionally comprising other VZV antigens.

4. A method of treating a patient suffering from or susceptible to Varicella Zoster virus infection as claimed in claim 3, wherein the other VZV antigens are selected from the group, gpI, gpII, gpIII, gpIV, gpV or IE62 or anchorless derivatives thereof.

5. A method of treating a patient suffering from or susceptible to Varicella Zoster virus infection as claimed in claim 1, additionally comprising an adjuvant.

6. A method of treating a patient suffering from or susceptible to Varicella Zoster virus infection as claimed in claim 5, wherein the adjuvant preferentially induces a TH1 response.

7. A method of treating a patient suffering from or susceptible to Varicella Zoster virus infection as claimed in claim 6, wherein the antigen is presented as an oil in water emulsion together with QS21 and 3D-MPL.

8. A method of producing a safe and effective immunogenic pharmaceutical composition comprising an isolated Varicella Zoster virus IE63 protein, or an isolated nucleic acid encoding a Varicella Zoster virus IE63 protein, comprising mixing said protein or said nucleic acid with a human pharmaceutically acceptable excipient.

9. A method as claimed in claim 8, wherein the excipient comprises an adjuvant.

* * * * *